United States Patent [19]

Scheiwe et al.

[11] Patent Number: 4,473,739
[45] Date of Patent: Sep. 25, 1984

[54] PROCESS AND APPARATUS FOR WARMING OF SUSPENSIONS OR SOLUTIONS FROZEN IN A FLAT PLASTIC BAG

[75] Inventors: Max-Werner Scheiwe; Günter Rau, both of Aachen, Fed. Rep. of Germany

[73] Assignee: Helmholtz-Institut für Biomedizinische Technik, Aachen, Fed. Rep. of Germany

[21] Appl. No.: 388,970

[22] Filed: Jun. 16, 1982

[51] Int. Cl.³ ............ B67D 5/62; F24H 1/12; A61F 5/14; H05B 1/02
[52] U.S. Cl. .................... 219/302; 366/146; 366/209; 219/385; 219/328
[58] Field of Search ............. 219/301, 302, 303–305, 219/296, 385, 308, 328; 604/113, 114; 128/399; 222/146 R, 146 HE, 146 H, 146 C; 165/46

[56] References Cited

U.S. PATENT DOCUMENTS

| | | | |
|---|---|---|---|
| 1,986,085 | 1/1935 | Weichal | 366/211 |
| 3,030,082 | 4/1962 | Matzen | 366/209 |
| 3,399,536 | 9/1968 | Walz | 219/302 |
| 3,475,590 | 10/1969 | Pins | 219/302 |
| 3,480,015 | 11/1969 | Gonzales | 219/301 |
| 3,590,215 | 6/1971 | Anderson | 604/114 |
| 4,117,881 | 10/1978 | Williams | 219/302 |
| 4,146,364 | 3/1979 | McCormick | 366/209 |
| 4,309,592 | 1/1982 | Le Boeuf | 219/302 |
| 4,356,383 | 10/1982 | Dahlberg | 219/302 |

Primary Examiner—B. A. Reynolds
Assistant Examiner—Teresa J. Walberg
Attorney, Agent, or Firm—Omri M. Behr

[57] ABSTRACT

There is provided an apparatus for warming aqueous suspensions or solutions of living cell substances contained in frozen form in a substantially flat plastic bag comprising two heater plates selectively movable against each other, which serve to receive the plastic bag containing the frozen sample, the temperature of these heater plates being programmable and the heater plates being supported by a holding device which is movable over a fixed base plate, this holding device being capable of being caused to swivel rhythmically in an elliptic direction by means of a swivelling device attached to it.

6 Claims, 6 Drawing Figures

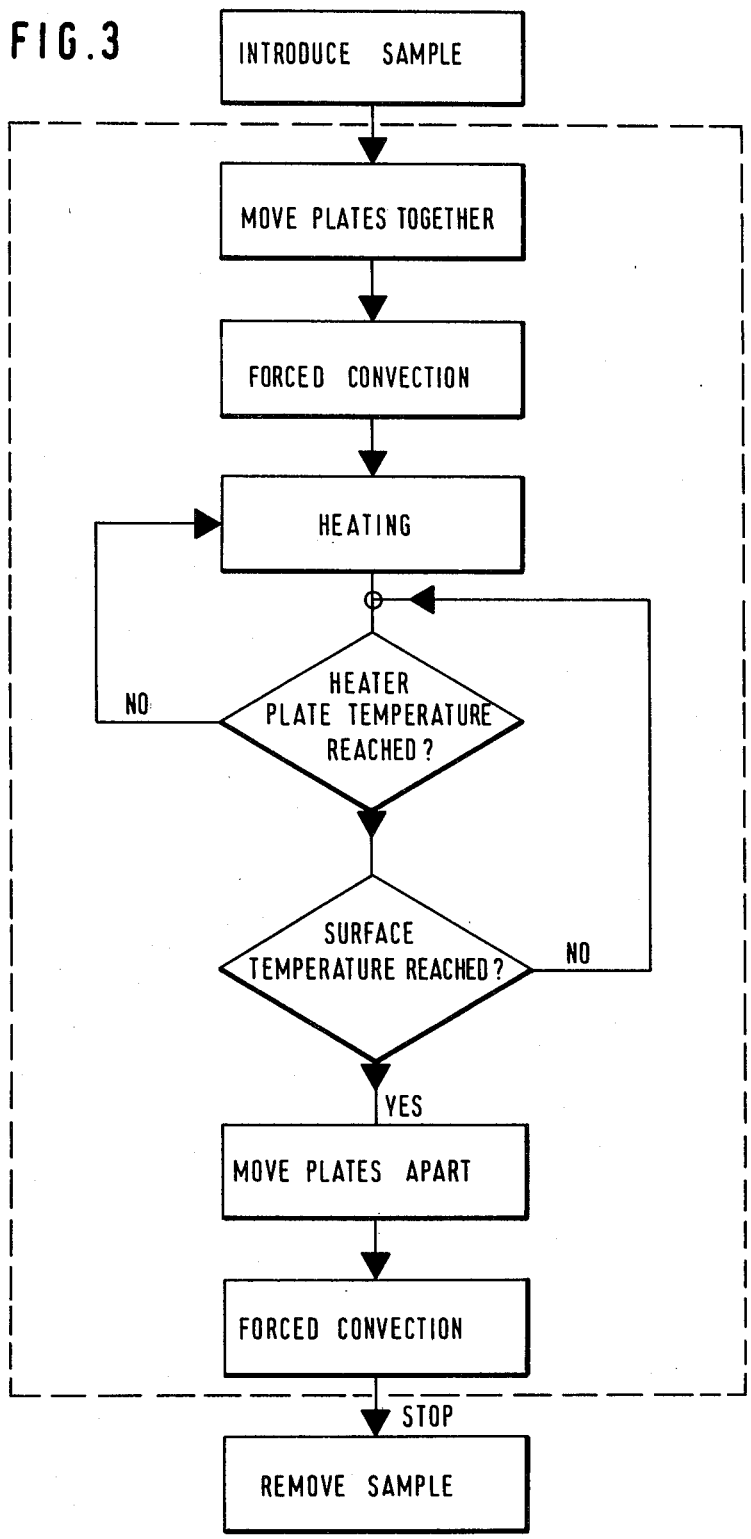

PROCESS AND APPARATUS FOR WARMING OF SUSPENSIONS OR SOLUTIONS FROZEN IN A FLAT PLASTIC BAG

BACKGROUND OF THE INVENTION

1. Field of the Invention

The present invention relates to a process and apparatus for warming of suspensions or solutions of living cell substance, such as units of human blood which are frozen in a flat plastic bag and which are called hereinafter freezing samples.

2. Description of the Prior Art

According to a known process, the use of larger quantities comprising a sample mass of approximately 50–500 g and the use of samples shaped into thin plates having a layer thickness of approximately 5–10 mm is common practice in order to obtain an economical quantity of frozen living blood cells and an economical yield of cryoglobulins. When using thin plates of this type, a uniform rate of temperature change, i.e. temperature change in relation to time, can be maintained within the limits of approximately 10% for almost the entire sample mass, except for the boundary layer. In common practice, the solutions discussed in the present disclosure are filled into a plastic bag which thereafter is heatsealed and frozen in a platelike holder in a way which is known in principle.

The rate of the temperature change during the warming process should be of the same order of magnitude as during the freezing process; however, a significantly more rapid warming rate as compared to the cooling rate is aimed at. Thereby devitrification and/or recrystallization and occurrence of intracellular ice for example inside frozen cells can be prevented. In the prior art, in order to avoid during the warming process a temperature gradient having a harmful effect between the ice block and the geometrical center of the plate and the boundary layer, forced convection is impressed upon the sample inside the bag by shaking. Thereby, on one hand the heat transfer to the melting ice is increased, and on the other hand overheating of particles close to the boundary of the aqueous solution is avoided.

Up until now, the warming process of the sample is carried out as follows:

Introduction of the sample which is frozen in a platelike bag into a water bath of e.g. 40° C.;
maintaining the melting sample in platelike shape during the process by means of special holders or containers, respectively;
moving of the sample with a frequency of approximately 4 Hz with an amplitude of approximately 8 cm in longitudinal direction;
after reaching an experimentally established predetermined time, removal of the bag from the water bath;
drying of the bag provided the sample is completely thawed and proceeding of the sample to further use.

The disadvantages of this known warming process are as follows:

1. The duration of time required for thawing during which the sample has to be immersed in the water bath is highly dependent on the mass of the sample. Even small variations of the mass in relation to an established mean value which are common in practice result in significant exceeding or falling below the temperature desired after thawing, e.g. +4° C. of the sample. Likewise, incomplete melting of the ice in the sample can be observed which may result in considerable damage to the quality of the material.

2. The handling of the samples can only be done by specially trained, qualified personnel as the positioning of samples frozen in the platelike bag during immersion in the water bath has to be done as rapidly as possible because the thawing process sets in immediately in full extent. The liquid occurring in the sample at this instant will deform the sample if it is not properly fixed. Rapid positioning is also important because as soon as the liquid occurs forced convection in the sample has to be started.

3. A special holder or container maintaining the sample in platelike shape is needed for the duration of the warming process. This necessitates the storage of each sample in appropriate containers beforehand which entails a considerable expenditure for each single sample or the locating of the sample in a container or holder after the sample has been introduced into the low temperature environment resulting in the well-known difficulties (such as ice formation, unintended warming of the sample, frost bites to the hands of the persons handling the sample) in particular when storing the material in liquid nitrogen as usual in medical practice.

4. The necessary drying of the sample after the thawing procedure represents additional work and loss of time. Drying of the bag is indispensable as normally ensuring handling under sterile conditions is foreseen; residues of water on the inlet and outlet connections would destroy sterility.

SUMMARY OF THE INVENTION

The purpose of the present invention, therefore, is to eliminate the drawbacks of the known process and to provide a process allowing the warming of aqueous suspensions or solutions which have been frozen in a flat plastic bag in a simple yet safe way. This purpose is achieved by the process according to the present invention as laid down in the claims.

The said process is carried out in the following way:

The samples which were each frozen in a platelike bag are warmed by means of electrical heat through heat conduction. For this purpose, the samples are placed between two metal plates which are heated by electrical current. The surface temperature $T_{OH}$ of these heater plates is set to a predetermined programmable value which may be in the range of 40° C. or higher. $T_{OH}$ is maintained at this value by means of a suitable generally known control device whith a maximum deviation in the range of 1° C. from the predetermined mean temperature being allowed for. During the warming process, the surface temperature $T_{OB}$ on the outside of the plastic bag is monitored continuously, this temperature being taken as indicator for the temperature $T_I$ inside the bag. For this purpose, solely knowledge of the thermal properties of the plastic foil constituting each individual bag is required; therefrom the temperature difference between $T_I$ and $T_{OB}$ can be calculated according to the respective heat transfer laws; the difference is in the order of magnitude of 5° C. The surface temperature $T_{OB}$ of the bag is preselected also and used for the termination of the heating process: as soon as $T_{OB}$ is reached the heater plates are removed from the sample. In addition, forced convection is impressed upon the freezing sample during the warming process by providing the entire system "heaterplate/freezing sample" with a corresponding relative motion. In order to increase the thermal heat transfer coefficient at the "ice-liquid" phase boundary in the partially thawed material, a special motion is impressed in a way in order to cause a flow of liquid, e.g. chiefly parallel to the ice front. To this end, the system "freezing sample - heater plate" is moved, e.g. elliptically. The motion frequency is in the range of $1 \div 10/s$, the inflection being in the range of $5 \div 20$ cm.

The advantages of the said process are manifold and of utmost importance for attaining the objective aimed at, namely qualitiy improvement and reproducibility of quality and results. It meets the requirements for defined temperature inside the warmed sample for safety in handling and independence of the exact mass of the freezing sample.

BRIEF DESCRIPTION OF THE DRAWINGS

FIG. 3 is a process flow diagram.

DESCRIPTION OF THE PREFERRED EMBODIMENTS

Figure 1:
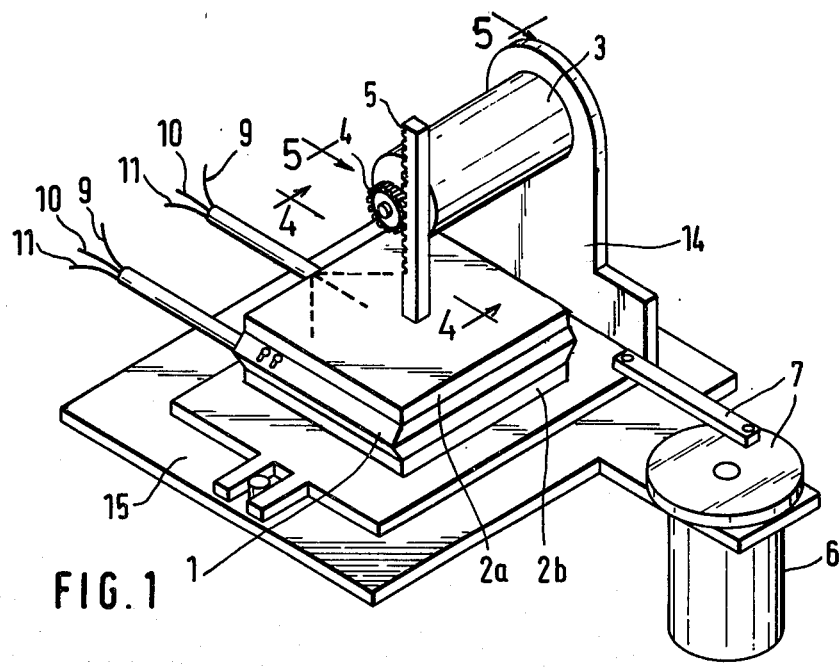
FIG. 1 is a downward perspective view of the apparatus of the invention.
Figure 4:
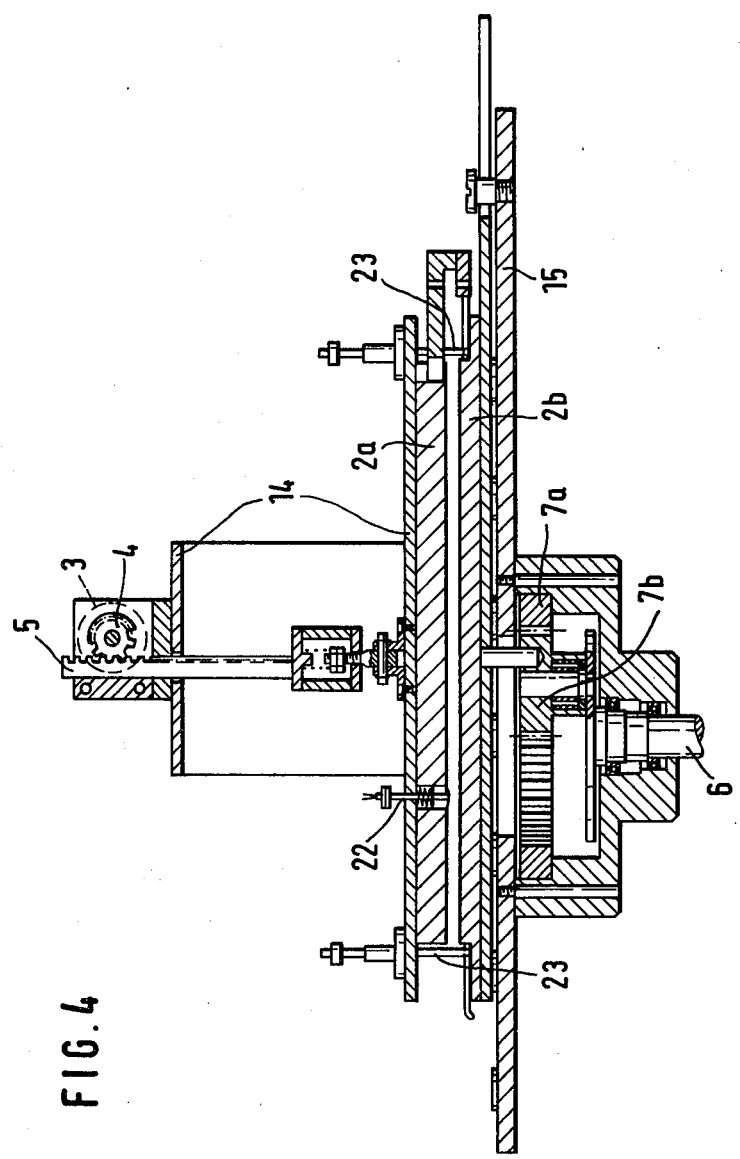
FIG. 4 is a cross-sectional side elevational view of the apparatus of FIG. 1 viewed from 4—4.
Figure 5:
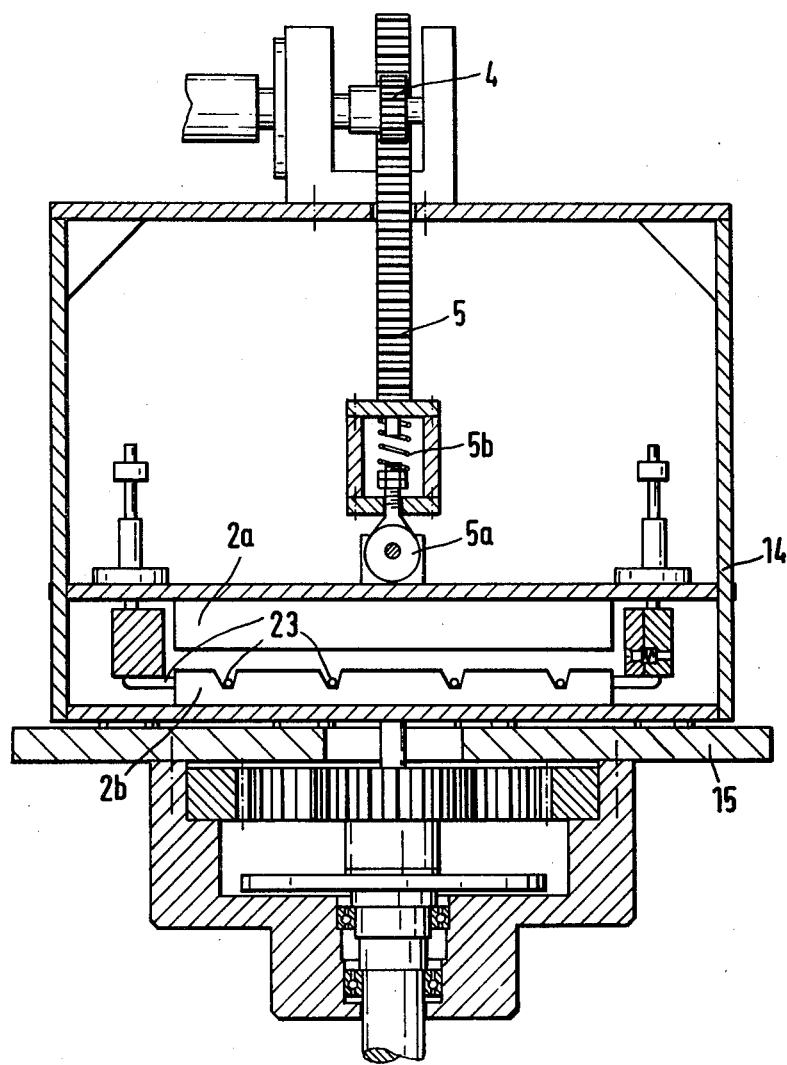
FIG. 5 is a cross-sectional front elevational view of the apparatus of FIG. 1 viewed from 5—5.

A technical arrangement can, for example, be done in the following way:

The plastic bag containing the freezing sample 1 (FIGS. 1, 4, 5) is placed between the heater plates 2a, 2b which are set apart. Thereby, a circuit is closed by means of a light barrier or mechanically causing the positioning motor 3 (servomotor 3) to move the heater plates together via pinion 4 and rack 5. The heater plate is pressed upon the plastic bag in a defined way by means of the springs 5b acting in the direction of the lifting. The rack and the heater plate are hinged together by the joint 5a at the end of the rack, the joint allowing the adjustment of the contact surface of the heater plate to freezing samples that are not exactly plane-parallel. The swivel-type motor 6 then sets in motion the holding device 14 via the circular base and connecting rod 7, and the planetary gear 7b and the sun gear 7a, respectively, thereby causing forced convection in the freezing sample at the start of the melting process, as set forth above, the holding device 14 being moved in relation to the base plate 15. Simultaneously, the heater plates are heated to the predetermined temperature $T_{OH}$. During the process, the temperature $T_{OH}$ of the heater plates, the temperature $T_{OB}$ of the freezing sample outside the foil bag and the proceeding melting of the ice are monitored through a mechanical probe in connection with a length gauge in the heater plates 2a and 2b by means of heat sensing probes 9a, 9b, 10a, 10b, and mechanical probes 11a, 11b. The thermal components consist of copperconstantan-thermocouples.

Figure 2A:
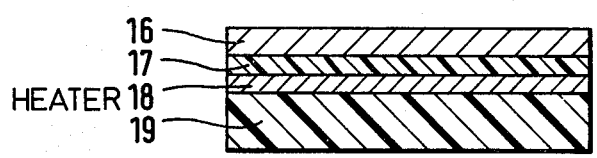
FIG. 2A is a cross sectional view of the heater plate segment.
Figure 2B:
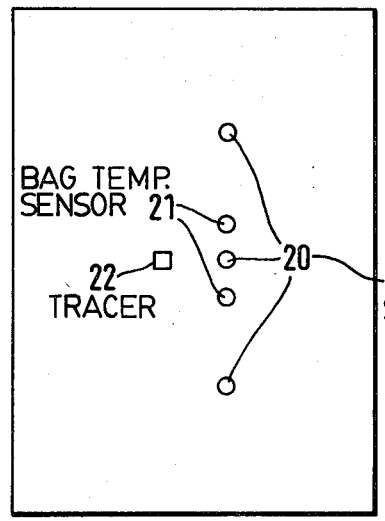
FIG. 2B is a plan view of the heater plates showing location of sensors and a mechanical tracer.

Inside the copper sheets 16 (FIG. 2), sensors 20 for measuring $T_{OH}$ are soldered; for measurin $T_{OB}$, surface probes 21 extend through the heater plate onto the plastic bag; the probes are spring-mounted and pressed upon the measuring points in order to allow the measurement of $T_{OB}$ with the least possible distortion. The mechanically operating tracer 22 is also spring-mounted and located in the freezing sample in such a way as to penetrate, as the melting proceeds, deeper into the already liquid solution. When ice is no longer present, the tracer extends through the full depth of the freezing sample and activates an acoustic and optical signal indicating the termination of the melting process. The warming process may thereby be terminated at this point. When the predetermined temperature $T_{OB}$ as indicator for the temperature of the freezing sample is reached, the motor 3 intended for lifting the sample is started, the plates are moved apart and simultaneously the freezing sample is lifted off the lower heater plate by means of a basket 23, moving upwards, in order to prevent a continued heating effect on the bag after the heater plate has been switched off. The swivel-type motor is then turned off and the sample is ready for subsequent use.

To avoid local overheating, the heater plates are constructed in the following way (FIG. 2):

The heating conductor sheet 18 (made for example of a material of the same class as thin copper conductor grid or other material of sufficiently high conductor resistivity like a grid made of stainless steel wire) is fixed to a thermally and electrically insulating plastic sheet 19 (made for example of a material of the same class as a phenolic laminated sheet). Over the heating conductor sheet 18 a thin electrically insulating sheet 17 (made for example of a material of the same class as epoxy resin or other material of sufficiently high thermal conductivity) is mounted. The contact to the freezing sample is established by means of the copper sheet 16, the extremely high heat conductivity of the latter balancing out local differences of heat transfer without adverse local temperature increase The process of adjustment between the mechanical components and the regulatory system can be seen in the flow chart, FIG. 3.

The advantages of the process according to the present invention for application on the warming of frozen aqueous solutions are:

1. Independence of the process of the mass of the sample as controlled heating and controlled termination of the total warming process are provided.
2. Preselection of a sample temperature and possible termination of the thawing process when the said temperature is reached. In many cases, the precise sample temperature is decisive for the quality of subsequent use of the material, as is well-known e.g. in the case of concentrates of living blood cells.
3. Defined forced convection in the sample, the resulting temperature field inside the sample being homogeneous in the desired way thus allowing the prevention of damaging devitrification or recrystallization and the ensuing damage to the cell membrane.
4. A saving in cost and time and gain in safety as no special container is needed to maintain the freezing sample in platelike shape during the warming process.
5. Introduction of the bag containing the frozen solution into the warming apparatus within the shortest possible time, thereby reducing the time of undefined warming in the ambient atmosphere by contact with air to such an extent that no quality loss occurs.

6. Execution of the warming process by auxiliary staff which in view of the increasing shortage of technical personnel in the medical field becomes increasingly important for the execution of the entire process.
7. Automated defined warming process by means of regulating and recording of the sample temperature and the temperature of the heater plates.
8. No drying of the sample needed thereby minimizing the danger of bacterial contamination.

Because of the advantages aforementioned, the warming process is particularly suited for sensitive biological cell concentrates and for the production process of cryoprecipitates from blood plasma or blood serum. For example, concentrates of frozen human bone marrow cells having a mass of 150 g are warmed by the said process from $-196°$ to $+4°$ C. within 60 s, the external thermal heat transfer coefficient being in the range of 200–600 W/qm K and a heating power of 4 KW being produced. An analogous process is applied to human lymphocytes, platelets and erythrocytes.

The prior art of warming using the aforementioned water bath technique is only of limited suitability for general application and for maintaining the desired quality of the substances in question. Both factors are taken into consideration by the process according to the present invention. Considering the economic importance of the provision of cryoglobulins and the growing tendency in clinics to store and administer separated cell fractions as cell concentrates obtained from units of whole blood, the progress achieved by the process according to the present invention will be of farreaching importance.

The following points are mentioned in summary:

The long-term preservation of aqueous suspensions of biological cells by cryogenic low temperature processes has gained a firm place nowadays, particularly in the medical field. In this place, not only the application of frozen red blood cells is to be mentioned, the storage and provision of which is done for a variety of reasons, such as use during surgery, for accidents and desasters, but also the completely novel and promising application recently made possible by the storage of units of blood for later retransfusion to the donor. Thus, tumor therapy can be decisively improved by retransfusion of bone marrow cells or lymphocytes and peripheral stem cells. An even greater demand for frozen units of platelets (thrombocytes) emerges provided sufficient quality of the frozen cells can be achieved.

An economically even more important scope of application of cryogenic preservation at low temperatures is possibly the application of cryogenic processes on aqueous solutions or suspensions for the production of cryoglobulins obtained from blood plasma, i.e. from the cell-free component of the blood for the economic provision of plasma-protein-fractions needed for immunological therapy measures and for prophylactic treatment.

The essential criterium for the applicability of both frozen cell concentrates and cryoglobulins obtained through low temperatures processes is the quality achieved at the end of the said process. In recent years, the influencing parameters that are to be optimized in order to achieve the highest possible yield of living cells and purified globulins respectively have become better known. In particular it stands out clearly that a strict dependence on
(a) the cooling rate, and
(b) the warming rate
of the freezing sample exists. Further parameters such as the addition of solutions to the liquid sample, the agents, e.g. cryoprotectants, influencing the behaviour of the sample during freezing; and the concentration and packing of the cells or globulins are the most important parameters mentioned. However, of decisive influence on the original quality of the treated sample are the aforementioned parameters (a) and (b).

What is claimed:

1. Apparatus for the warming of aqueous suspensions or solutions of living cell substances contained in frozen form in a substantially flat plastic bag comprising two heater plates (2a, 2b) selectively movable against each other, which serve to receive the said plastic bag (1) containing the said frozen sample, the temperature of the said heater plates being programmable and the said heater plates being supported by a holding device (14) which is movable over a fixed base plate (15) the said holding device being capable of being caused to swivel rhythmically in elliptic direction by means of a swivelling device attached thereto.

2. Apparatus according to claim 1, further comprising measuring instruments (20, 21, 22) which, during the said warming process, monitor the surface temperature of both the said heater plates (2a, 2b) and the outside of the said plastic bag (1).

3. Apparatus according to claim 2, wherein said measuring instruments further comprise spring-mounted surface probes which extend through one of the said heater plates (2a) and press upon the said plastic bag (1) in order to monitor the surface temperature of the said plastic bag.

4. Apparatus according to claim 2, comprising mechanically operated spring-mounted probes pressing upon the said plastic bag (1) containing the said frozen sample capable of activating a signal as soon as the said frozen sample is completely thawed.

5. Apparatus according to claim 2, comprising means actuated by said measuring instruments, for causing the two heater plates to move apart and the frozen sample to be lifted off the lower heater plate (2b) as soon as the predetermined temperature has been reached.

6. Apparatus according to claim 2, wherein the said heater plates each comprise a thermally and electrically insulting plastic sheet (19) which is fixed to a heating conductor sheet (18) onto which first a thin electrically insulating sheet (17) and a second copper sheet (16) are fixed.

* * * * *